United States Patent [19]

Miyazawa

[11] Patent Number: 4,492,476
[45] Date of Patent: Jan. 8, 1985

[54] DEFECT DETECTING METHOD AND APPARATUS

[75] Inventor: Takashi Miyazawa, Funabashi, Japan

[73] Assignee: Kirin Beer Kabushiki Kaisha, Tokyo, Japan

[21] Appl. No.: 347,745

[22] Filed: Feb. 10, 1982

[30] Foreign Application Priority Data

Feb. 20, 1981 [JP] Japan .................................. 56-23895
Feb. 2, 1982 [JP] Japan .................................. 57-15395

[51] Int. Cl.³ ............................................. G01N 21/90
[52] U.S. Cl. .................................. 356/428; 250/223 B
[58] Field of Search ........................ 356/240, 428, 427; 250/223 B, 563, 572; 358/101, 106

[56] References Cited

U.S. PATENT DOCUMENTS 4,376,951 3/1983 Miyazawa ....................... 356/240 X
4,378,495 3/1983 Miller ............................... 250/223 B Primary Examiner—Vincent P. McGraw
Assistant Examiner—Samuel A. Turner
Attorney, Agent, or Firm—Ladas & Parry

[57] ABSTRACT

In a defect detecting method and apparatus, the image of a bottle under inspection, which is conveyed while being spun, is divided into picture elements arranged in a matrix form, signals representative of the picture elements are generated sequentially and repeatedly, and the signals of the picture elements, on the same imaginary line perpendicular to the central axis of the image, are compared with each other, and the result of the comparison is used to detect a defect such as a foreign matter or a scratch.

27 Claims, 8 Drawing Figures

DEFECT DETECTING METHOD AND APPARATUS

BACKGROUND OF THE INVENTION

This invention relates to a method of detecting defects such as foreign matters, scratches and cracks included in bottles such as beer bottle and juice bottles, and to an apparatus for practicing the method.

A variety of techniques have been proposed in the art in which a bottle under inspection is conveyed while being spun, and the optical image of the bottle is converted into electrical signals from which defects included in the bottle are detected. One example of the techniques is disclosed in Japanese Patent Application No. 120073/1978 which has been filed by the present applicant. The technique disclosed therein has advantages over the techniques known before. It is however sometimes felt that the technique is sometimes insufficient in reliability.

SUMMARY OF THE INVENTION

Accordingly, an object of this invention is to provide a defect detecting method in which bottles can be inspected for defects with higher reliability, and an apparatus for practicing the method.

According to one aspect of the invention, there is provided a defect detecting method in which:

a bottle under inspection is conveyed while being spun, picture element signals respectively corresponding to a plurality of picture elements, arranged in a matrix form, of an image of the bottle are generated sequentially and repeatedly, and the picture element signals of picture elements which are on the same imaginary line perpendicular to the central axis of the image are sequentially subjected to comparison to detect a defect in the bottle.

According to another aspect of the invention, there is provided a defect detecting apparatus which comprises:

conveying means for conveying and spinning a bottle under inspection;

picture element signal generating means for sequentially and repeatedly generating picture element signals corresponding to a plurality of picture elements, arranged in a matrix form, of an image of the bottle being conveyed;

memory means for storing at least some of the picture element signals generated by the picture element signal generating means; and discrimination means responsive to the picture element signals from the picture element signal generating means or the memory means, for sequentially comparing the picture element signals of picture elements which are on the same imaginary line perpendicular to the central axis of the image, to detect a defect in the bottle.

DETAILED DESCRIPTION OF THE INVENTION

Figure 1:
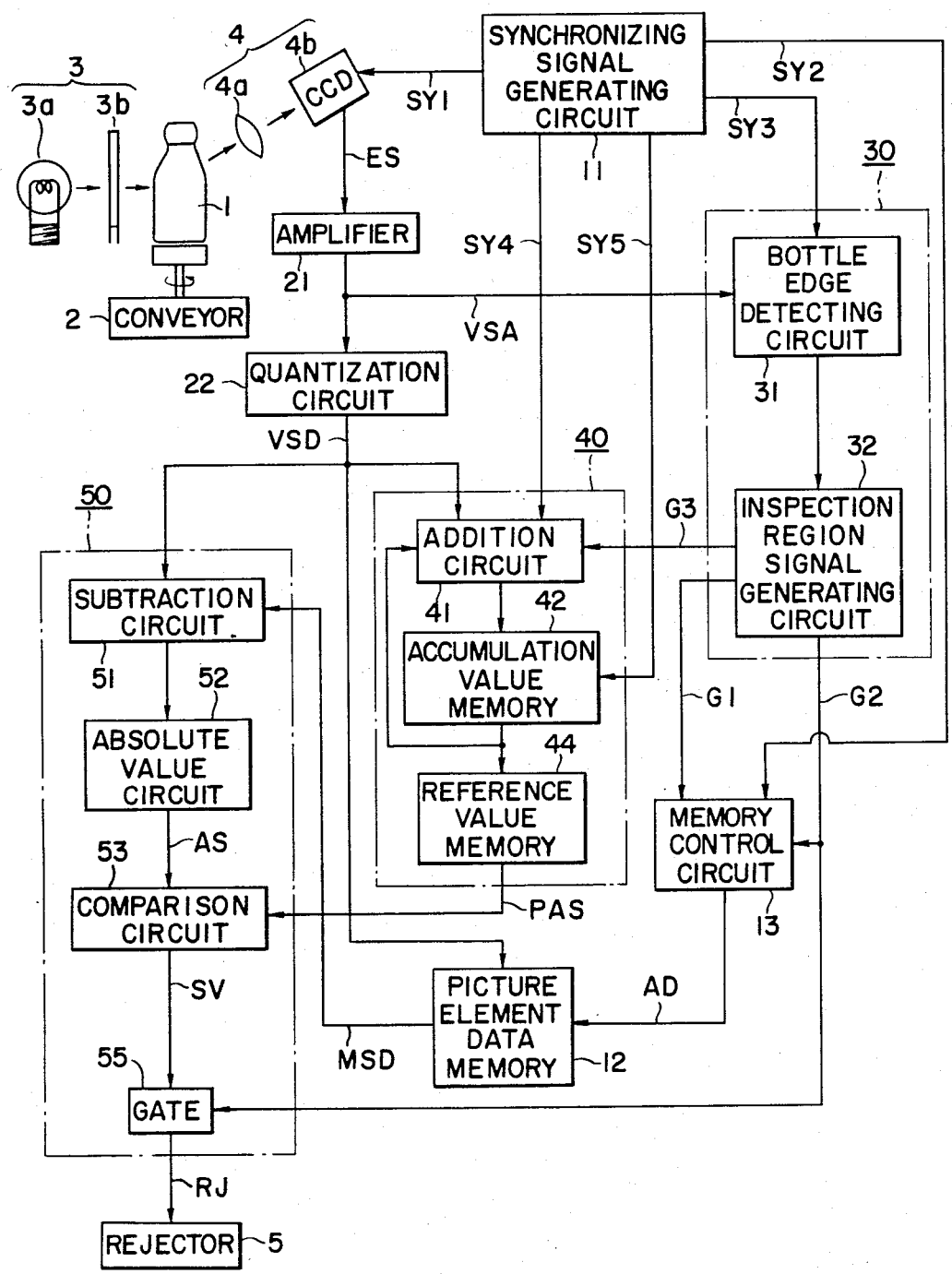
FIG. 1 is a block diagram showing one embodiment of a defect detecting apparatus according to this invention.
Figure 2:
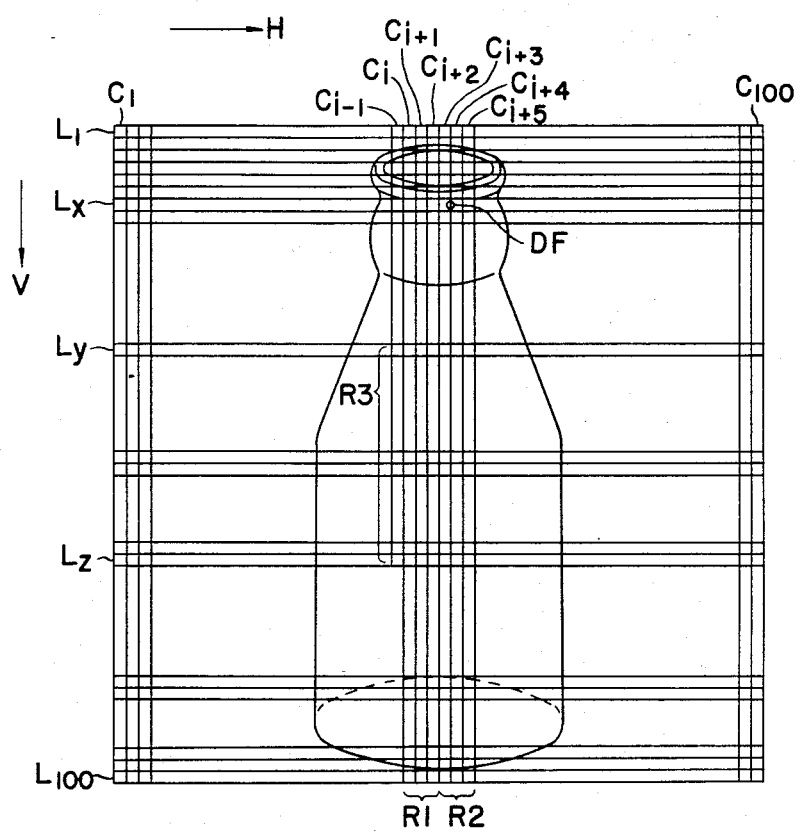
FIG. 2 is a schematic diagram showing the image of a bottle under inspection and how the image is divided into picture elements.

In FIG. 1 which shows one embodiment of a defect detecting apparatus according to this invention, reference numeral 1 designates a bottle to be inspected which is conveyed by a conveyor 2 while being spun; 3 designates an illuminating unit for illuminating the bottle 1, the unit 3 comprising a lamp 3a and a diffusion plate 3b which is disposed between the lamp 3a and the bottle 1, for diffusing light from the lamp 3a; and 4 designates an image pickup unit which is arranged so that the bottle 1 is set between the unit 4 and the illuminating unit 3. The image pickup unit 4 comprises: a lens system 4a for forming the image of a bottle; and a photo-electric converter for producing an electrical signal corresponding to the brightness of each of the picture elements of the image thus formed. The photo-electric converter 4b is so arranged that its main scanning direction (in which scanning is carried out with higher frequency) is in parallel with the central axis of the image of the bottle 1. The photo-electric converter 4b may be a CCD (charge-coupled device) two-dimensional image sensor. The CCD two-dimensional image sensor is composed of a light receiving section having a plurality of light receiving elements arranged in matrix form and having the light receiving surfaces at the image-formed position, and an accumulation section having a plurality of accumulating elements in correspondence to the plurality of light receiving elements. The light receiving elements produce electric charges corresponding to the brightness of the picture elements of the image. The electric charges are transferred to the corresponding accumulating elements, and are then shifted therein and outputted. Since the shifting mentioned above is equivalent to scanning of the accumulating elements, sequentially outputting (reading) the signals from the accumulating elements is sometimes referred to as "scanning". The direction of the main scanning is in parallel with the central axis of the image of the bottle, while the direction of the auxiliary scanning is perpendicular to the central axis. Accordingly, as shown in FIG. 2, the reading is carried out in the order of columns $C_1$, $C_2$, $C_3$ and so on, beginning with the upper left corner. Receiving of light and generating of electric charges in the light receiving section and scanning of the accumulation section are carried out in a parallel, i.e., simultaneously. Before each frame is scanned, the electric charges are transferred from the light receiving section to the accumulation section. In the light receiving section, the light receiving elements are arranged in a matrix pattern of 100 rows×100 columns, for instance.

Figure 4:
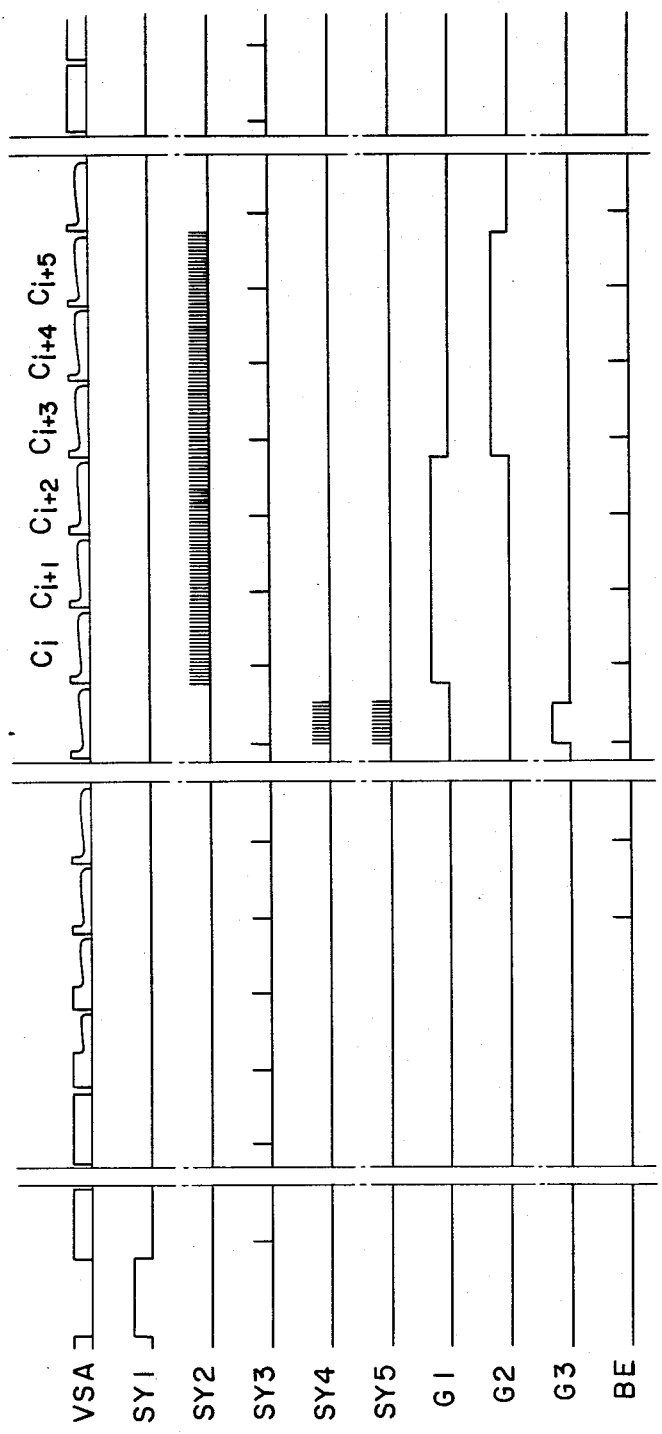
FIG. 4 is a time chart indicating various signals which appear in the apparatus in FIG. 1.

Further in FIG. 1, reference numeral 11 designates a synchronizing signal generating circuit which produces synchronizing signals SY1 through SY5 as shown in FIG. 4, which synchronize the operations of the image pickup unit 4 and other circuits (described later); 21 designates an amplifier for amplifying analog picture element signals ES which are sequentially outputted by the image pick-up unit 4, to provide an analog picture element signal VSA; and 22 designates a quantization circuit for quantizing the analog picture element signal VSA outputted by the amplifier 21, for instance into sixty four levels. The quantization is carried out with the timing which is determined by the synchronizing signal from the synchronizing signal generating circuit 11.

Of the devices described above, the image pickup unit 4, the amplifier 21 and the quantization circuit 22 form a picture element signal generating device for sequentially and repeatedly generating picture element signals corresponding to a plurality of picture elements, arranged in a matrix form, of an image of the bottle being conveyed.

An inspection region determining circuit 30 receives the signal VSA from the amplifier 21 and the synchronizing signal SY3 from the synchronizing signal generating circuit 6, and determines an inspection region. The circuit 30 comprises an edge inspecting circuit 31 and an inspection region signal generating circuit 32. The circuit 31 receives the picture element signal VSA and the synchronizing signal SY3, and detects a part of the picture element signal which corresponds to the edge of the bottle image. This inspection is carried out according to the fact that light passed through the bottle is considerably less intense than light which reaches the image pickup unit without passing through the bottle. Among the picture element signals VSA which are obtained by sequentially scanning the light receiving elements, those in a predetermined row are extracted with the aid of the synchronizing signal SY3, and when the level thereof becomes lower than a predetermined value, the picture element signal at that instant is detected as corresponding to the bottle edge. Upon detection of the bottle edge, the bottle edge detecting circuit 31 outputs a bottle edge signal BE. The inspection region signal generating circuit 32 may comprise a combination of delay circuits. The circuit 32 generates a gate signal G3 which rises, after the scanning advances by a predetermined number of picture element columns after reception of the bottle edge signal BE, and when the scanning advances to the picture element which is in a predetermined row, and which falls when scanning advances by a predetermined number of picture elements after the rise. Furthermore, the inspection region signal generating circuit 32 generates gates signals G1 and G2 each of which rises when the scanning advances by a predetermined number of picture element columns after reception of the bottle edge signal BE and which falls when the scanning advances by a predetermined number of picture element columns after the rise.

The gate signals G3, G1 and G2 are at a "high" level when regions R3 (picture elements of rows $L_y$-$L_z$ of column $C_{i-1}$), R1 (the picture element columns $C_i$-$C_{i+2}$) and R2 (the picture element columns $C_{i+3}$-$C_{i+5}$) are scanned, respectively. The timing of the gate signals G1 and G2 is so determined that, among the separation lines between the picture element columns, one between the picture element columns $C_{i+2}$ and $C_{i+3}$, i.e., the border line between the regions R1 and R2 is nearest to (or substantially coincides with) the central axis of the image of the bottle 1. The sum of the regions R1 and R2 is an inspection region for detecting defects. The presence or absence of defects is determined from comparison of picture elements in the inspection region.

Figure 3:
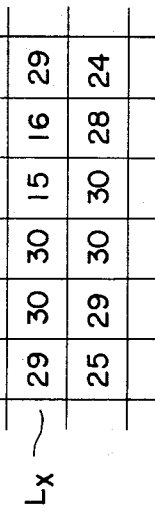
FIG. 3 is a diagram showing one example of the values of picture element signals obtained by the use of the apparatus shown in FIG. 1.

FIG. 3 shows one example of the values of signals of the picture elements in the regions R1 and R2 (indicating the brightnesses of the corresponding parts of the bottle image). In the example, the values of signals of the picture elements at the intersections of row $L_x$ and columns $C_{i+3}$ and $C_{i+4}$ are smaller because of the presence of a defect.

The inspection region (R1+R2) is a belt-shaped area which extends along the central axis, as was described above. Therefore, if the inspection is carried out on the picture elements signals of one frame only, then it is impossible to detect defects outside the inspection region. However, according to the invention, the bottle is spun or turned at least a full turn while being in the field or range of vision of the image pickup unit 4, and while the bottle is being spun, the picture element signals of many frames can be obtained. Accordingly, the entire circumference of the bottle is inspected by combining all the frames with respect to the belt-shaped inspection region.

Referring back to FIG. 1, reference numeral 12 designates a picture element data memory; and 13 designates a memory control circuit. Among the picture element signals outputted by the quantization circuit 22, those specified by the memory control circuit 13, i.e., those corresponding to the picture elements in a region R1 indicated by the inspection region signal G1 are stored in the picture element data memory 12. The addresses where the picture element signals are to be stored are specified by the memory control circuit 13. Thus, the picture element data are written therein in the order of columns $C_i$, $C_{i+1}$, $C_{i+2}$, beginning with the top of each column, for instance. Under the control of the memory control circuit 13, the picture element data are outputted from the memory 12 to a subtraction circuit 51 (described later). The picture element data are read out in the order of columns $C_{i+2}$, $C_{i+1}$, $C_i$, beginning with the top of each column. In writing and reading the picture element data, the memory 12 is addressed with the timing which is determined by the synchronizing signal SY2.

The subtraction circuit 51 receives the output data of the quantization circuit 22 and the output data of the picture element data memory 12, and obtains the difference therebetween. When the quantization circuit 22 outputs the signals of the picture elements in columns $C_{i+3}$, $C_{i+4}$ and $C_{i+5}$ in the region R2, the picture element data memory 12 outputs the data of the picture elements in columns $C_{i+2}$, $C_{i+1}$ and $C_i$ in the region R1. In other words, the signals of picture elements which are symmetrical with respect to one of the seperation lines closest to, and hence substantially coincident with the central axis of the image are subjected to comparison to obtain the difference therebetween, and the picture element signals used for the comparison by the subtraction circuit 51 are of the picture elements closer to the said separation line than a predetermined distance, i.e. the width of three columns.

The output of the subtraction circuit 51 is applied to an absolute value circuit 52, where its absolute value is obtained.

A reference value signal generating circuit 40 in FIG. 1 receives the picture element signal VSD from the quantization circuit 22 and the inspection region signal G3 from the inspection region signal generating circuit 32, to detect the brightness of a bottle under inspection, to output a reference value signal. In the reference value signal generating circuit 40, an addition circuit 41 and an accumulation value memory 42 cooperate to accumulate the values of the picture elements in the region G3. The result of accumulation of all the picture elements in the region R3 of a frame is supplied to a reference value memory 44 where it is converted into a corresponding reference value. In other words, the reference value memory 44 receives as an address the signal from the accumulation value memory 42 and outputs the content at the address as the reference value. This reference value signal is used for comparison in a comparator 53 (described later) until the accumulation value of the next frame and a new reference value according thereto are determined. When the bottle 1 has a low optical transparency, the accumulation value is small and the reference value PAS is also small. Adding data in the addition circuit 41 and storing data in the accumulation value memory 42 are carried out with the timing which is determined by the synchronizing signals SY4 and SY5.

In the comparison circuit 53, the output AS of the absolute value circuit 52 is compared with the output PAS of the reference value memory 44. When the former is larger than the latter, the comparison circuit 53 outputs a defect signal SV.

A gate 55 is opened by the region signal G2. When the defect signal SV is applied to the gate 55 thus opened, it is outputted, as a rejection signal RJ, to a bottle rejecting unit 5.

The above-described subtraction circuit 51, absolute value circuit 52, comparison circuit 53, and gate 55 form a discriminating circuit 50 which discriminates the presence or absence of a defect according to the picture element signals VSD and MSD and the reference value signal PAS.

Upon receipt of the rejection signal RJ, the bottle rejecting circuit 5 rejects the bottle under inspection.

As was described before, the image pickup unit 4 scans the image in its range or field of vision repeatedly and generates the picture element signals of the frames sequentially and repeatedly. When a bottle 1, being conveyed by the conveyor 2, comes in the range of the image pickup unit 4, the bottle edge is detected by the bottle edge detecting circuit 31. According to the position of the bottle edge thus detected, the inspection region R3 for determining the reference value and the inspection regions R1 and R2 for detecting defects are determined. The signals of the picture elements in the region R3 are applied to the reference value signal generating circuit 40, where the reference value signal PAS is formed. The signals of the picture elements in the region R1 are stored in the picture element data memory 12, and are then read out of the memory 12 when the signals of the picture elements in the region R2 are applied to the subtraction circuit 51 from the quantization circuit 22. In this case, the signal of the picture element at the intersection of column $C_{i+3}$ and a row is compared with the signal of the picture element at the intersection of column $C_{i+2}$ and the same row; the signal of the picture element at the intersection of column $C_{i+4}$ and a row is compared with the signal of the picture element at the intersection of column $C_{i+1}$ and the same row, the signal of the picture element at the intersection of column $C_{i+5}$ and a row is compared with the signal of the picture element at the intersection of column $C_i$ and the same row. That is, the signals of picture elements which are symmetrical with respect to the separation line substantially coincident with the central axis of the image are subjected to comparison. In general, the signals of such symmetrical picture elements are substantially equal, as shown in FIG. 4. Therefore, the difference between the signals is small, and the absolute value thereof is smaller than the reference value PAS. On the other hand, if the bottle has a defect DF, the signals of the picture elements corresponding to the defect DF are much smaller than the signals of the picture elements which are symmetrical therewith, and therefore the difference therebetween is large and the absolute value thereof is larger than the reference value PAS.

The operations of the subtraction circuit 51, the absolute value circuit 52 and the comparison circuit 53 are carried out for each of the picture elements in the region R2; that is, the operations are carried out, for each frame, as many times as the number of picture elements in the region R2.

The above-described operations are carried out whenever a new frame occurs, and are repeated as long as a bottle is in the range of the image pickup unit 4. While being in the range of the image pick-up unit 4, the bottle makes at least one turn. Therefore, as the bottle is spun, the images of many frames are obtained. Thus, the entire circumference of the bottle is inspected before the bottle goes out of the range of the image pickup unit.

In the above-described embodiment, the picture elements which are used to determine the reference value PAS is in the region R3 adjacent to the region R1. However, the region R3 may be spaced apart from the region R1, or a part of all of the region R3 may overlap that of the region R1. Furthermore, it is not always necessary that the picture elements for determining the reference value are in a unitary region (such as R3). For instance, the picture elements may be those dispersed over the image. In addition, it is not always required that the picture elements for determining the reference value of the bottle are those of the same frame as used for comparison in the subtraction circuit 51. For instance, the picture elements may be those which are obtained when only a part of the bottle is in the range of the image pickup unit. That is, all that is necessary is that the reference value is determined before the signals of the picture elements in the regions R1 and R2 are subjected to comparison.

In the case where the brightness of a bottle is substantially constant, the reference value signal generating circuit 40 can be eliminated and a constant reference value is employed.

In the above-described embodiment, only the signals of the picture elements in the region R1 are stored in the picture element data memory 12, and they are subjected to comparison sequentially when the signals of the picture elements in the region R2 are outputted through the quantization circuit 22. However, the signals of the picture elements in the regions R1 and R2 may be stored in the picture element data memory 12, and thereafter they may be read out in any order (for instance, in such a manner that the signals of picture elements which correspond to a part of a bottle where a defect exists at a higher probability are read out first) for comparison. Furthermore, all the picture element signals produced by the photo-electric converter 4b may be stored in the picture element data memory, and thereafter they are read out for whatever purposes they may be required for.

In the above-described embodiment, the subtraction circuit 51 is employed to obtain the difference between two picture element signals; however, instead of the subtraction circuit 51, a division circuit may be used to obtain the ratio of two picture element signals. Thus it will be appreciated that one of the features of the invention resides in comparison between two picture element signals and judgement that a defect exits if the result of the comparison (difference, ratio, or the like) exceeds the reference value.

The invention has been described with respect to the case where the image pickup unit is so positioned as to "see" a bottle from obliquely above. Such an arrangement is particularly advantageous when inspecting the mouth portion of a bottle or the bottom portion of a bottle. However, the image pickup unit may be positioned so as to see a bottle from the side thereof.

Figure 5:
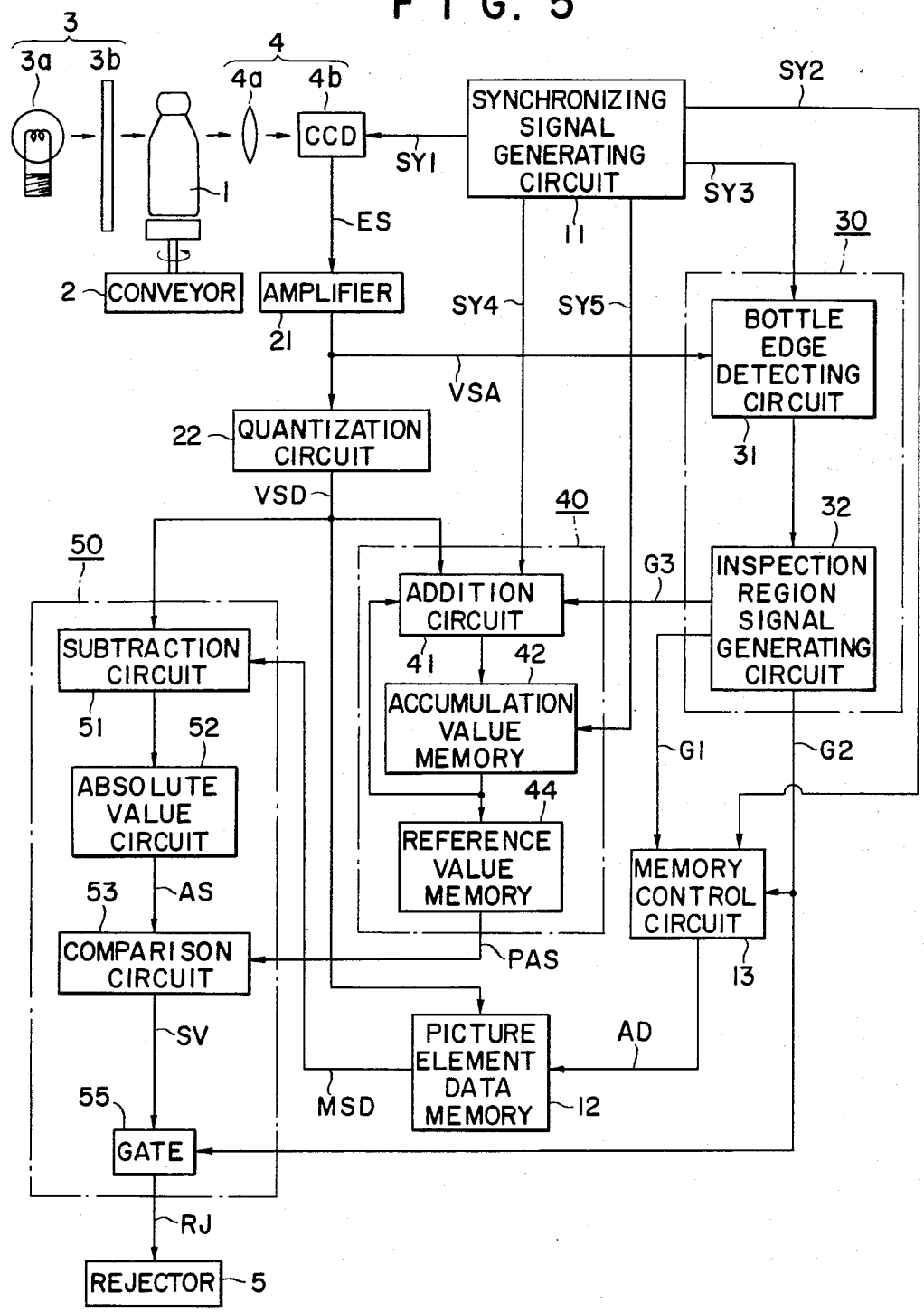
FIG. 5 is a block diagram showing a second embodiment of the defect detecting apparatus according to the invention.
Figure 8:
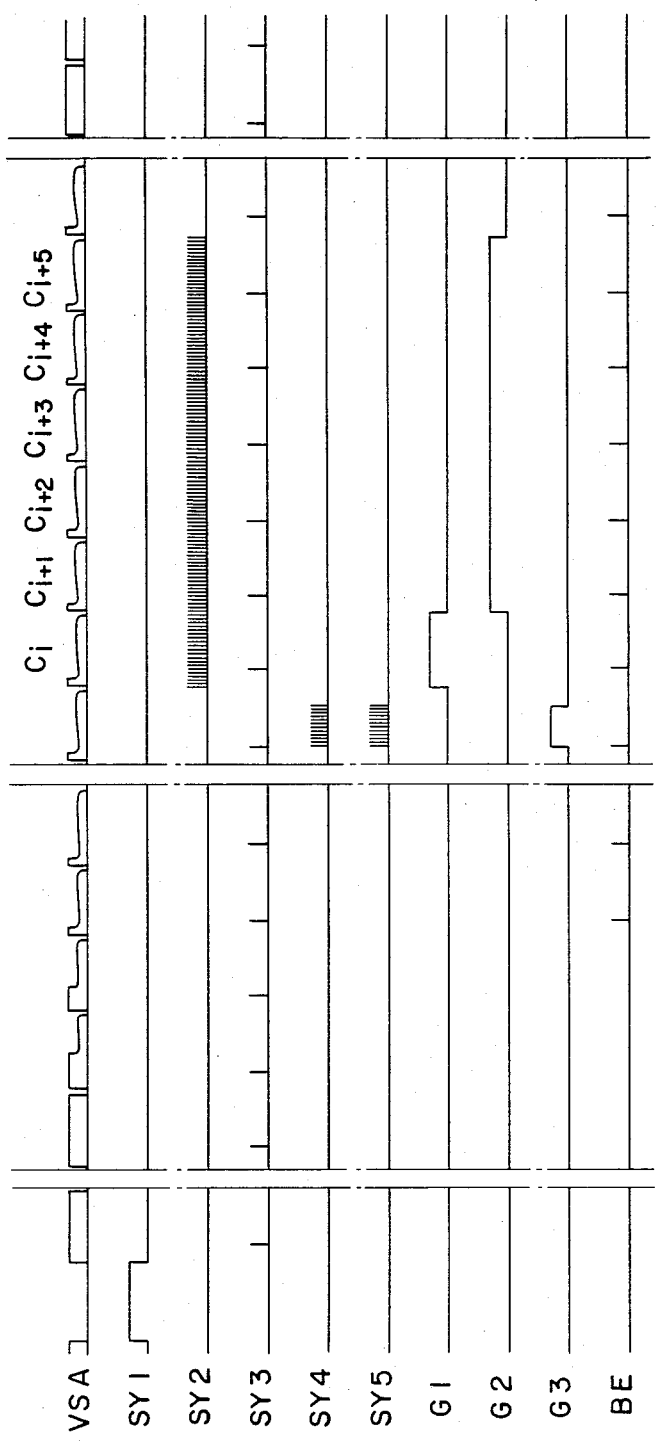
FIG. 8 is a time chart showing various signals which appear in the apparatus shown in FIG. 5.

FIG. 5 shows another embodiment of the apparatus according to the invention. In this embodiment, an image pickup unit 4 is set to see or shoot a bottle 1 from the side thereof. Among the signals of picture elements of the image of the bottle 1, only the signals of picture elements in the first column $C_i$ in the inspection region are stored in a picture element data memory 12. In a subtraction circuit 51, the signals of picture elements in column $C_i$ and in the respective rows are compared with the signals of picture elements at the intersections of other columns $C_{i+1}$ through $C_{i+5}$ and in the same row. An inspection region signal generating circuit 32 generates inspection region signals G1 and G2 as shown in FIG. 8. While the inspection region signal G1 is applied to a memory control circuit 13, the latter 13 operates to cause the picture element data memory 12 to store the picture element signals from a quantization circuit 22. Furthermore, while the inspection region signal G2 is applied to the memory control circuit 13, the latter 13 operates to cause the picture element data memory 12 to output the signals of picture elements in the same line as that of the picture elements of the signals outputted by the quantization circuit 22. The signals of picture elements is outputted by the picture element data memory 12 repeatedly as long as the quantization circuit 22 outputs the signals of picture elements in columns $C_{i+1}$ through $C_{i+5}$. The operations of the remaining circuit elements are similar to those in the apparatus shown in FIG. 1.

Figure 7:
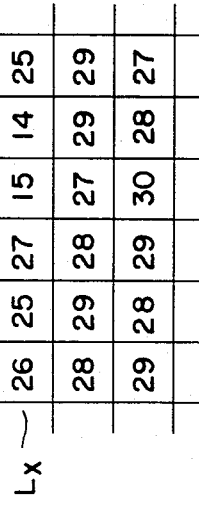
FIG. 7 is a diagram showing one example of the values of picture element signals obtained by the use of the apparatus shown in FIG. 5.
Figure 6:
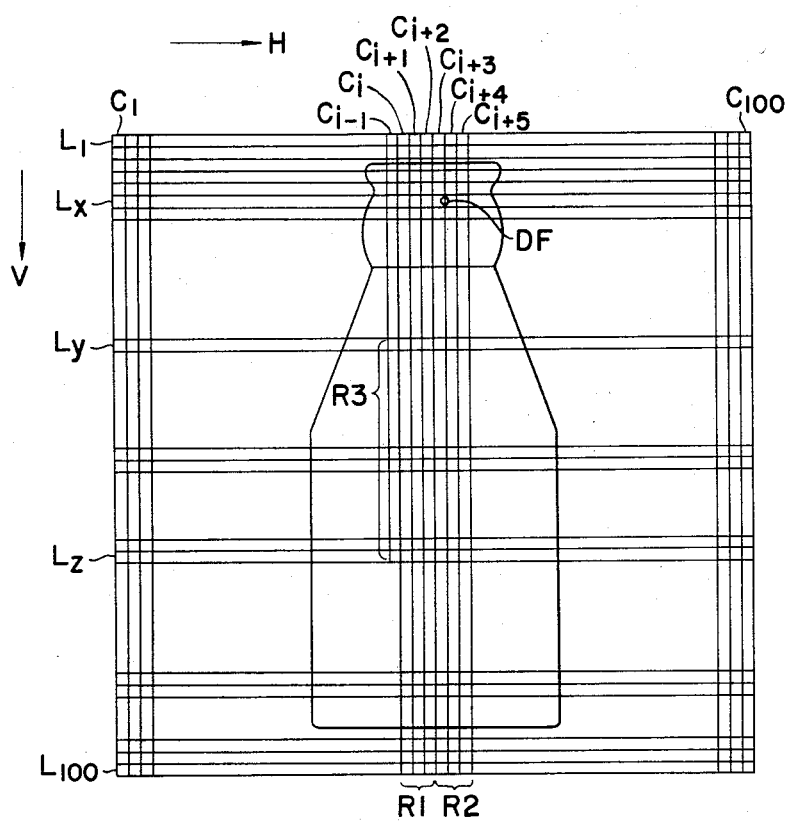
FIG. 6 is a schematic diagram showing the image of a bottle under inspection and how the image is divided into picture elements.

Assume that, as shown in FIG. 6, a bottle includes a defect DF corresponding to the intersections of columns $C_{i+3}$ and $C_{i+4}$ and row $L_x$, and the values of the picture element signals are as shown in FIG. 7. When the quantization circuit 22 outputs the picture element signal which is defined by the intersection of column $C_{i+3}$ and row $L_x$, and the picture element signal thus outputted is compared with the picture element signal which is defined by the intersection of column $C_i$ and row $L_x$ in the subtraction circuit 51; and when the quantization circuit 22 outputs the picture element signal which is defined by the intersection of column $C_{i+4}$ and row $L_x$, and the picture element signal thus outputted is compared with the picture element signal which is defined by the intersection of column $C_i$ and row $L_x$ in the subtraction circuit 51; the absolute values of the outputs of the subtraction circuit 51, i.e. the outputs of the absolute value circuit 52 are larger than the reference value PAS from the reference value memory 44. Thereupon, the comparison circuit 53 outputs the defect signals SV which are applied through the gate 55 to the bottle rejecting unit.

In the example shown in FIG. 5, the picture element data memory 12 can sufficiently operate if it has a capacity of storing the signals of picture elements in one column.

Modifications which can be applied to the embodiment shown in FIG. 1 is also applicable to the embodiment of FIG. 5. For instance, the picture element region used to determine the reference value is not limited to the area R3 indicated in FIG. 6, and the reference value signal generating circuit 40 amy be eliminated.

Moreover, in the embodiment of FIG. 5 the signals of picture elements other than those in column $C_i$ may be stored in the picture element data memory 12, and instead of the subtraction circuit 51, a division circuit may be used. Furthermore, in the case where the bottle conveying speed is relatively low, instead of the image pickup unit with a two-dimensional image sensor, an image pickup unit with a one-dimensional image sensor may be employed.

The defect detecting apparatuses shown in FIGS. 1 and 5 may be used separately; however, they may be used in combination. In the latter case, the apparatuses may be arranged so that, while the apparatus in FIG. 1 inspects the mouth of a bottle, the apparatus in FIG. 5 inspects the barrel of the bottle.

The techniques described with reference to FIGS. 1 and 5 may be utilized in combination with other defect detecting techniques.

What is claimed is:

1. A defect detecting method comprising the following steps:
    a bottle under inspection is conveyed while being spun,
    picture element signals respectively corresponding to a plurality of picture elements, arranged in a matrix form, of an image of said bottle are generated sequentially and repeatedly, and
    the picture element signals of picture elements which are on a same imaginary line perpendicular to a central axis of said image are sequentially subjected to comparison to detect a defect in said bottle,
    wherein the picture element signal of one picture element is compared with the picture element signal of another picture element that is symmetrical with respect to the central axis of said image to detect a defect in said bottle,
    the central axis being an axis parallel to an axis about which the bottle is spun.

2. A method as claimed in claim 1, in which the picture element signals used for the comparison are of picture elements closer to the central axis of said image than a predetermined distance.

3. A method as claimed in claim 1, in which the picture element signals of picture elements which are symmetrical with respect to one of separation lines which is closest to the central axis of said image, said separation lines separating, from one another, columns of picture elements aligned in the direction of the central axis of said image.

4. A method as claimed in claim 1, in which said image is one obtained by seeing said bottle from obliquely above.

5. A method as claimed in claim 1 or 2, in which the picture element signals of picture elements in one of columns of picture elements aligned in the direction of the central axis of said image are compared with the picture element signals of picture elements in another column.

6. A method as claimed in claim 1, in which the sequential generation of picture element signals is repeated while said bottle is spun at least a full turn.

7. A defect detecting method comprising the following steps:
   a bottle under inspection is conveyed while being spun,
   picture element signals respectively corresponding to a plurality of picture elements, arranged in a matrix form, of an image of said bottle are generated sequentially and repeatedly, and
   the picture element signals of picture elements which are on the same imaginary line perpendicular to the central axis of said image are sequentially subjected to comparison to detect a defect in said bottle,
   wherein the picture element signals of picture elements in one of columns of picture elements aligned in the direction of the central axis of said image are compared with the picture element signals of picture element in another column.

8. A method as claimed in claim 7, in which the picture element signals used for the comparison are of picture elements closer to the central axis of said image than a predetermined distance.

9. A method as claimed in claim 7, in which the picture element signals of picture elements which are symmetrical with respect to one of separation lines which is closest to the central axis of said image, said separation lines separating, from one another, columns of picture elements aligned in the direction of the central axis of said image.

10. A method as claimed in claim 7, in which said image is one obtained by seeing said bottle obliquely from above.

11. A method as claimed in claim 7, in which the sequential generation of picture element signals is repeated while said bottle is spun at least a full turn.

12. A defect detecting apparatus which comprises:
    conveying means for conveying and spinning a bottle under inspection;
    picture element signal generating means for sequentially and repeatedly generating picture element signals corresponding to a plurality of picture elements, arranged in a matrix form, of an image of said bottle being conveyed;
    memory means for storing at least some of the picture element signals generated by said picture element signal generating means; and
    discrimination means responsive to the picture element signals from said picture element signal generating means or said memory means, for sequentially comparing the picture element signals of picture elements which are on the same imaginary line perpendicular to the central axis of said image, to detect a defect in said bottle,
    wherein said discrimination means compares the picture element signal of one picture element with the picture element signal of another picture element that is symmetrical with respect to the central axis of said image,
    the central axis being parallel to the axis about which the bottle is spun.

13. An apparatus as claimed in claim 12, in which said discrimination means compares the picture element signals of picture elements which are symmetrical with respect to one of separation lines which is closest to the central axis of said image, said separation lines separating, from one another, columns of picture elements aligned in the direction of the central axis of said image.

14. An apparatus as claimed in claim 12, in which said discrimination means compares the picture element signals of the picture elements in one of columns of picture elements aligned in the direction of the central axis of said image with the picture element signals of picture elements in another picture element column.

15. An apparatus as claimed in claim 12 or 14, in which said discrimination means compares, with each other, the picture element signals of two picture elements in one of rows of picture elements arranged to extend perpendicularly to the central axis of said image.

16. An apparatus as claimed in claim 12, in which said picture element signal generating means comprises an image pickup unit which is disposed to see said bottle from obliquely above, to produce said signals of picture elements.

17. An apparatus as claimed in claim 16, in which said image pickup unit has a photo-electric converter which has a main scanning direction in parallel with the central axis of said image.

18. An apparatus as claimed in claim 16 or 17, in which said picture element signal generating means comprises a quantizing circuit for quantizing an output signal of said image pickup unit.

19. An apparatus as claimed in claim 12, wherein said bottle is spun at least a full turn while it is in the range of said picture element signal generating means.

20. An apparatus as claimed in claim 12, further comprising reference value signal generating means responsive to the output of the picture element signal generating means for generating a reference value signal, and wherein said discrimination means judges that a defect exists if the result of said comparison exceeds said reference value.

21. A defect detecting apparatus which comprises:
    conveying means for conveying and spinning a bottle under inspection;
    picture element signal generating means for sequentially and repeatedly generating picture element signals corresponding to a plurality of picture elements, arranged in a matrix form, of an image of said bottle being conveyed;
    memory means for storing at least some of the picture element signals generated by said picture element signal generating means; and
    discrimination means responsive to the picture element signals from said picture element signal generating means or said memory means, for sequentially comparing the picture element signals of picture elements which are on the same imaginary line perpendicular to the central axis of said image, to detect a defect in said bottle,
    wherein said discrimination means compares the picture element signals of the picture elements in one of columns of picture elements aligned in the direction of the central axis of said image with the picture element signals of picture elements in another picture element column.

22. An apparatus as claimed in claim 21, in which said discrimination means compares, with each other, the picture element signals of two picture elements in one of rows of picture elements arranged to extend perpendicularly to the central axis of said image.

23. An apparatus as claimed in claim 21, in which said picture element signal generating means comprises an image pickup unit which is disposed to see said bottle from obliquely above, to produce said signals of picture elements.

24. An apparatus as claimed in claim 23, in which said image pickup unit has a photo-electric converter which has a main scanning direction in parallel with the central axis of said image.

25. An apparatus as claimed in claim 23 or 24, in which said picture element signal generating means comprises a quantizing circuit for quantizing an output signal of said image pickup unit.

26. An apparatus as claimed in claim 21, wherein said bottle is spun at least a full turn while it is in the range of said picture element signal generating means.

27. An apparatus as claimed in claim 21, further comprising reference value signal generating means responsive to the output of the picture element signal generating means for generating a reference value signal, and wherein said discrimination means judges that a defect exists if the result of said comparison exceeds said reference value.

* * * * *